United States Patent [19]

Fürste

[11] 4,410,243

[45] Oct. 18, 1983

[54] ARRANGEMENT FOR TEST IMAGE ROTATION IN REFRACTOMETERS

[76] Inventor: Dietmar Fürste, 3, Carl-Zeiss-Platz, Jena, German Democratic Rep.

[21] Appl. No.: 163,269

[22] Filed: Jul. 14, 1980

[30] Foreign Application Priority Data

Jul. 24, 1979 [DD] German Democratic Rep. ... 214565

[51] Int. Cl.³ .............................................. A61B 3/10
[52] U.S. Cl. .................................... 351/211; 351/214
[58] Field of Search .................... 351/13, 10, 15, 6, 9, 351/11, 12

[56] References Cited

U.S. PATENT DOCUMENTS 4,125,320 11/1978 Rassow et al. ..................... 351/13

Primary Examiner—John K. Corbin
Assistant Examiner—Rodney B. Bovernick

[57] ABSTRACT

The invention relates to an arrangement for rotating test images in refractometers for physical determination of defects of sight of a patient's eye. The arrangement is based upon the coincidence principle and has a folded path of beams to obtain a compact construction. The test images and the Scheiner apertures are mounted in rotatable sleeves (mounts) and each rotation of the sleeve of the test image is transferred to the sleeve of the Scheiner apertures by respective gear means, thus a test mark offered to a patient's eye is simultaneously rotated with the Scheiner apertures. In this manner an easy handling of the refractometer at a high precision is ensured.

5 Claims, 1 Drawing Figure

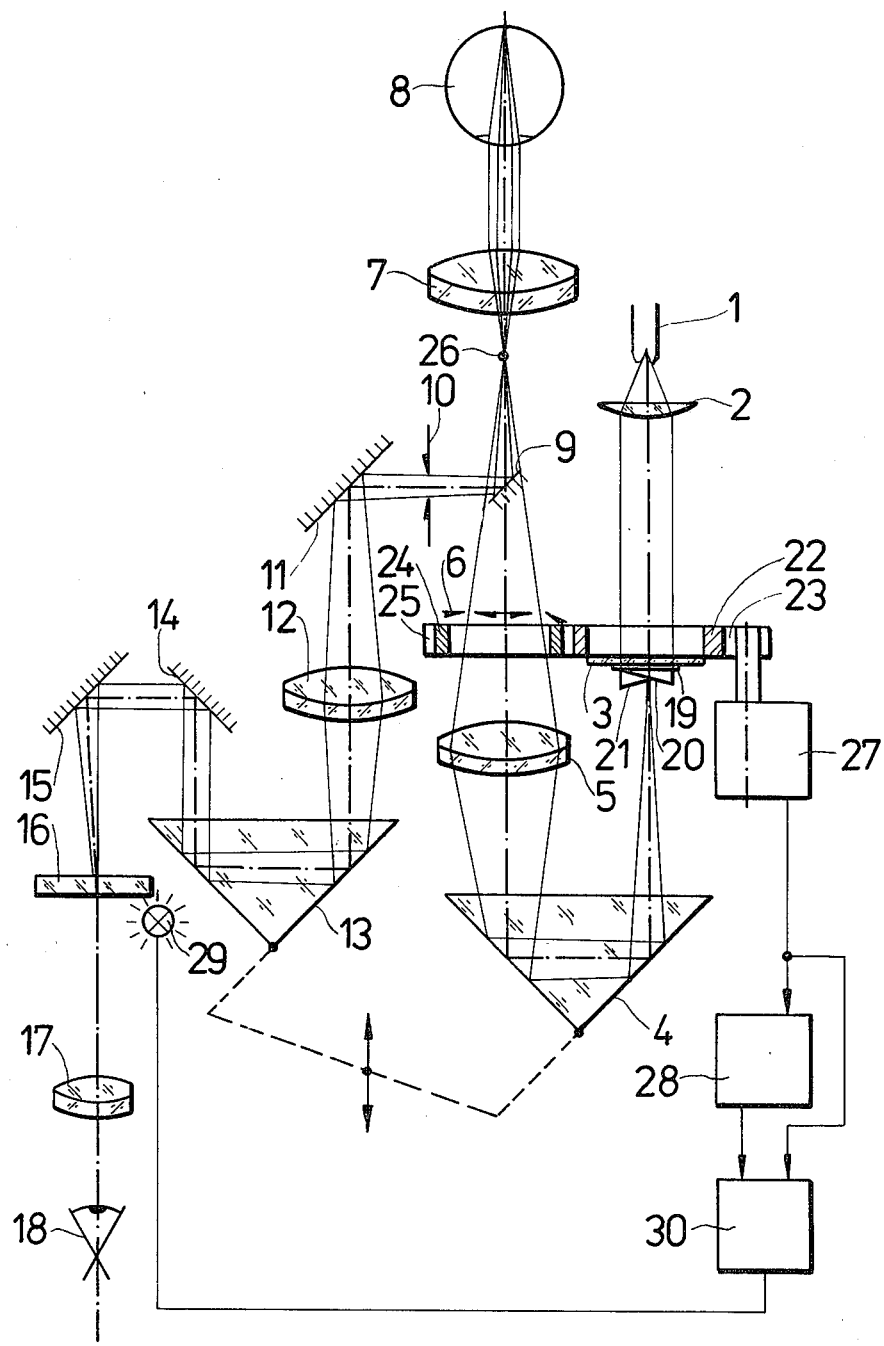

ARRANGEMENT FOR TEST IMAGE ROTATION IN REFRACTOMETERS

The invention relates to a refractometer for physical determination of the defective sight of a patient's eye, operating according to the coincidence measuring principle, that is, under use of a Scheiner illumination. The path of beams of said refractometer is folded to obtain a compact construction.

Devices of this kind project a test marking image upon the retina of a patient's eye at a simultaneous observation through a telescope.

Two seperate paths of beams for observation and projection are used to eliminate interfering reflections during the observation. The test mark image is, in turn, projected via a split illumination path for producing, in a first step, two semi-images of the testing mark on the retina in the event of any defective sight of a patient's eye.

Then the eye is optically offered an intermediate image of the test mark at a finite adjustable distance for measuring the defect of sight so that the two semi-images can fuse to one mark image upon the retina of the defectively sighted eye. Such a coincidence of the semi-images is obtained at a distance of the intermediate test images from the eye at which the keenness of vision is ascertained for an unaided eye without accomodation. The resulting distance of the test mark intermediate image is a measure for the defect of sight and can be read at a calibrated scale provided at the device.

When testing for astigmatism it is necessary to obtain the principal axes which is achieved by rotating the test mark image. A compact construction of the device is obtained by folding the illumination path and the observation path by use of prisms or reflectors. There are refractometers known which operate according to the coincidence measuring principle, that is, the illumination path is split up.

The test marks and the Scheiner apertures, required for splitting, however, are rigidly arranged in these devices so that the entire device has to be rotated when the test image requires rotation. Such a performance is time consuming and cumbersome. Another known kind of refractometers already provides means for rotating the test image. These devices both, rotate the test figure physically provided in the device in a rotatable mount as well as fold the illumination path. They, however, do not employ the measuring principle of coincidence. The device is adjusted by focusing the test mark image upon the retina under use of an annular bright field aperture. These devices are disadvantageous due to the limited measuring precision.

It is an object of the present invention to obviate the above disadvantages.

It is a further object of the present invention to provide a refractometer for use in ophthalmology which is easy to handle, has a considerably high measuring precision and operates on the coincidence measuring principle, that is, according to the Scheiner type of illumination.

It is still a further object of the present invention to rotate a test mark image in the device itself.

These and other objects are realised in an ophthalmologic refractometer of the Scheiner type and in which light paths are folded, comprising two rotatable mounts within which a test mark and a Scheiner aperture, respectively, are arranged. Each rotation of the test mark mount is transferred to the Scheiner aperture mount by gear means in such a manner that the sense of rotation of the illumination path which is folded by reflections is the same for the test mark and the Scheiner aperture. Hence, the rotation of the image of the test mark and of the image of the Scheiner aperture are simultaneously effective in the pupil of the patient's eye through the rotation of the illumination path.

It is advantageous to measure continously the rotations of the rotatable mounts by an electric angular position detector and to store the resulting values.

It is a further advantage when a newly set and measured value indicative of a new angular position of the mounts is compared to the previously obtained value in an electronic comparator circuit and a corresponding signal is delivered to an instrument which offers a visible signal to the operator when the new angular position has arrived at 90° compared to the stored value.

Said instrument is provided in the device according to the invention in the field of view of the operator so that the latter is optically informed when a new desired value is obtained.

In order that the invention may be more readily understood reference is made to the accompanying drawing which illustrates diagrammatically and by way of example one embodiment thereof and where the FIGURE is a schematic view of the inventional arrangement.

A condenser 2 produces an image of a lamp coil of a light source 1 at infinity. The resulting parallel bundle of light illuminates a glass-plate 3, which is arranged in a central opening of a rotatable mount 22 and to which a test mark 19 and two cemented wedges 20 and 21 are attached. The mount 22 carries an external toothed rim 23. The bundle of parallel light is split into two partial light bundles (not shown) which pass a prism 4 and an objective 5, the latter imaging two images of the lamp coil 1 into two openings of a Scheiner aperture 6, which is arranged in a central opening of a rotatable mount 24 provided with an external toothed rim 25. The Scheiner aperture 6 is arranged in the focal plane of the non-displaceable objective 5. The latter images the test mark 19 into a place 26, which is to be found in the focus of an ophthalmoscope lens 7 or displaced by a definite amount in front or in the rear of said lens 7, depending on the position of a displaceable prism 4 employed for focussing. The ophthalmoscope lens 7 in cooperation with the optical system of a patient's eye under investigation produces an image of the intermediate image of the test mark 19 located at 26 upon the retina of the eye 8. This image upon the retina is, in turn, imaged upon a graduated plate 16 through the aperture 10, via the reflectors 9 and 11, a non-displaceable objective 12, a prism 13 coupled to the prism 4 both being commonly displaceable and the reflectors 14 and 15. Said image is observed by the operator 18 via an eyepiece 17. The prisms 4 and 13 are of identical shape and size and are displaced in dependence on the defect of sight of the patient's eyes by equal amounts.

The displacement serves to focus the device and, at the same time, is a measure of the defect of sight of the patient's eyes.

The defect of sight can be read from a not shown display attached to one of the two prisms 4 and 13.

Since the objectives 5 and 12 are of identical construction, it is ensured that the test image projected upon the retina of the eye 8 is imaged upon the graduated plate 16 at each position of the prisms 4 and 13.

The ophthalmoscope lens 7 images the apertures 6 and 10 into the pupil of the eye 8, the aperture 6 having the effect of a Scheiner aperture with two openings through which the split illumination path is directed for producing the two semi-images of the test marks.

In the pupil of the eye 8 the apertures 6 and 10 are imaged into a plane spaced apart by a small distance which permits to seperate the observation path from the illumination path, as desired, so that an observation is feasible without any interferences by reflections.

In operation, the test image offered the patient's eye 8 is rotated by the toothed rims 23 and 25, the mounts 22 and 24 of which include the test mark 19 and the Scheiner aperture 6, respectively. The counter rotations of the two meshing toothed rims 23 and 25 are optically realised through the properties of the prism 4, that is, a light beam which enters the prism 4 clockwise rotated will leave the same under counterclock rotation. According to the invention the arrangement is so dimensioned that the lamp coil is imaged sufficiently enlarged into the plane of the Scheiner aperture 6 by the combination of the condenser lens 2 and the objective 5 so that the aperture openings of said aperture 6 are always sufficiently illuminated and light losses are substantially eliminated. Since the lamp coil 1 is neither mechanically nor optically rotated the image thereof maintains its orientation relative to the optical axis even when the illumination path is rotated.

One of the toothed rims 23 and 25, respectively, is provided with a not shown scale for reading the angular positions of the rotated test mark 19. Since two measurements per eye have to be carried out at two mutually perpendicular positions of the test mark 19 when the axis has to be measured in the event of astigmatism of the eye 8, and, since the angular position of the axial cross relative to the horizontal line is only known after the measurement, it is of advantage to provide a signal to the operator informing him that the test mark has been rotated exactly by 90° between the first measurement and the second measurement.

This is achieved in that the position of the toothed rims 23 and 25 is constantly scanned by an electric angular position detector 27, the operation of which is generally known. After the first measurement the angular position detector 27 delivers a signal corresponding to the measured angular value after a respective delivery command and feeds this signal into an electronic storage 28 followed by a comparator 30.

The test mark is then rotated by 90° in the course of the second measurement.

The achieved angular value provided from the angular position detector 27 is compared to the previous one stored in the storage 28 and a signal is produced exactly when a 90° rotation is obtained. This signal is applied to a luminescent diode 29, which is arranged adjacent to the graduated plate 16, and said diode 29 lights thus signalizing to the operator that the desired 90° rotation is obtained.

In this manner the conventional time consuming storing and calculating of the new angular value is eliminated.

What I claim is:

1. An arrangement for test image rotation in refractometers employing Scheiner apertures, comprising subsequently and in optical alignment
   a light source for emitting a bundle of light,
   a collector lens for paralleling said bundle of light,
   a first rotatable mount being provided with a central opening coaxially in and relative to said bundle of light,
   a transparent member substantially at right angles to said bundle of light,
   a test marking,
   two optical wedges adjacently arranged to and in a plane parallel to a plane defined by the transparent member and having the refracting edges in mutual opposition,
      said transparent member covering said central opening of said first mount,
      said test marking being attached to said transparent member,
      said two optical wedges splitting said bundle of parallel light into two partial bundles of light,
   and further comprising in optical alignment,
   a second rotatable mount being provided with a central opening,
   a Scheiner aperture being coaxially arranged in said central opening of said second rotatable mount,
      said first and said second rotatable mount being arranged in said plane and being provided with an external toothed rim each, and mutually meshing via the toothed rims,
   a first prism,
   a second prism,
      said first prism and said second prism being connected to each other via mechanical means for simultaneous displacement by equal amounts,
      said first prism being arranged in said two partial bundles of light subsequent to said two wedges for deviating said partial bundles substantially about 180°,
   a first objective lens being arranged between said first prism and said second rotatable mount in said two partial bundles of light for imaging the latter from said first prism into the two openings of said Scheiner aperture, and ophthalmoscope lens subsequently to said Scheiner aperture and
   a patient's eye,
   both being subsequently arranged in said two partial bundles of light,
      said ophthalmoscope lens having a focal point,
      said first objective lens producing an intermediate image of said test marking substantially in the focal point of said ophthalmoscope lens,
      said ophthalmoscope lens imaging said test marking upon the retina of the patient's eye for producing a retina test marking image,
   a semi-transparent reflector,
   a first reflector,
   a second objective lens,
      said semi-transparent reflector being transparent to and inclinedly inserted into the two partial bundles of light between said Scheiner apertures and said ophthalmoscope lens and reflective to the retina test marking image bundle of light,
      said semi-transparent reflector directing said retina test marking image bundle of light substantially at right angles to said two partial bundles of light from said ophthalmoscope lens to said second objective lens,
      said first reflector being inclinedly inserted into said retina test marking image bundle of light and directing the latter substantially in parallel and spaced relation to said two partial bundles of light from said semi-transparent reflector to said second objective lens, said second objective lens being arranged in said retina test marking image bundle of light between said first reflector and said second prism, a second reflector following said second objective lens, a third reflector, a graduated plate, an eyepiece, said second reflector, said third reflector, said graduated plate and said eyepiece being subsequently arranged in said retina test marking image bundle of light, said second prism being for directing and folding said retina test marking image bundle of light from said second objective lens to said second reflector, said second and said third reflector being inclinedly arranged in and relative to said retina test marking image bundle of light for folding the latter by substantially 180°, said graduated plate being for indicating said retina test marking image, said eyepiece being for observation of said graduated plate.

2. An arrangement for test image rotation as claimed in claim 1, wherein drive means are provided, connected to said first and second rotation mount, respectively, for imparting a rotation and counterrotation, respectively, to said first and second rotation mount.

3. An arrangement for test image rotation as claimed in claim 2, wherein an angle detector is connected to said rotation means for detecting the angular position of said first relative to said second rotation mount, said detector being connected to an electronic storage means and to an electronic comparator.

4. An arrangement as claimed in claim 3, wherein said electronic storage means is connected to said comparator.

5. An arrangement for test image rotation as claimed in claim 4, wherein indicator means are provided indicative of a desired angular position of said first rotation mount relative to said second rotation mount, said indicator means being connected to said comparator.

* * * * *